United States Patent [19]
Merkle et al.

[11] Patent Number: 5,847,154
[45] Date of Patent: Dec. 8, 1998

[54] METHOD OF PREPARING 1,2-DIMETHYL-3, 5-DIARYLPYRAZOLIUM METHYLSULFATES

[75] Inventors: Hans Rupert Merkle, Ludwigshafen; Erich Fretschner, Neckarsteinach, both of Germany

[73] Assignee: BASF Aktiengesellschaft, Ludwigshafen, Germany

[21] Appl. No.: 981,925

[22] PCT Filed: Jul. 26, 1996

[86] PCT No.: PCT/EP96/03316

§ 371 Date: Jan. 13, 1998

§ 102(e) Date: Jan. 13, 1998

[87] PCT Pub. No.: WO97/06148

PCT Pub. Date: Feb. 20, 1997

[30] Foreign Application Priority Data

Aug. 8, 1995 [DE] Germany ................... 195 29 056.9

[51] Int. Cl.[6] .................................................. C07D 231/10
[52] U.S. Cl. ................................ 548/373.1; 548/375.1; 548/377.1
[58] Field of Search ........................ 548/373.1, 375.1, 548/377.1

[56] References Cited

U.S. PATENT DOCUMENTS 3,882,142   5/1975   Walworth et al. ................. 260/311
3,910,949   10/1975  Stepek et al. ..................... 260/311

OTHER PUBLICATIONS

Organic Chemistry, 403, (1920).
Organic Chemistry, 539, (1920).
Derwent Abst, JP 690037700 (690517).

Primary Examiner—Johann Richter
Assistant Examiner—Jane C. Oswecki
Attorney, Agent, or Firm—Keil & Weinkauf

[57] ABSTRACT

A process for the preparation of 1,2-dimethyl-3,5-diarylpyrazolium methylsulfates of the formula I

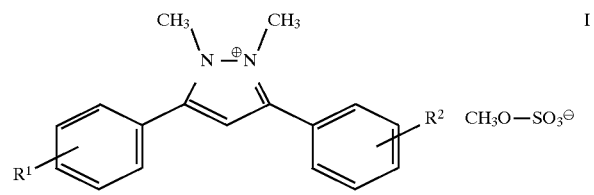

where $R^1$ and $R^2$ independently of one another are hydrogen, $C_1$–$C_4$-alkyl, $C_3$–$C_8$-cycloalkyl, $C_1$–$C_4$-alkoxy, halogen, nitro, $C_1$–$C_4$-haloalkyl or aryl all of which are inert under the reaction conditions, in which 1-methyl-3,5-diarylpyrazoles of the formula II

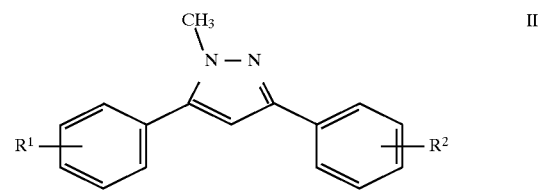

where $R^1$ and $R^2$ have the abovementioned meanings are reacted with a) methanol and $SO_3$, b) methanol and sulfuric acid or optionally, c) methanol and methylsulfuric acid elevated temperatures.

4 Claims, No Drawings

METHOD OF PREPARING 1,2-DIMETHYL-3,5-DIARYLPYRAZOLIUM METHYLSULFATES

This application is a 371 of PCT/EP96/03316 filed Jul. 26, 1996.

The present invention relates to a novel process for the preparation of 1,2-dimethyl-3,5-diarylpyrazolium methylsulfates of the formula I

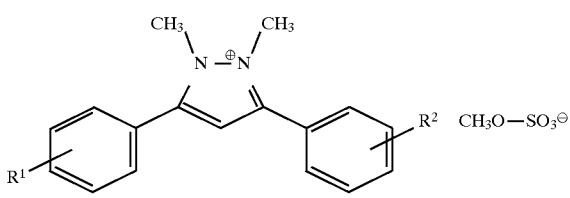

where $R^1$ and $R^2$ independently of one another are hydrogen, $C_1$–$C_4$-alkyl, $C_3$–$C_8$-cycloalkyl, $C_1$–$C_4$-alkoxy, halogen, nitro, $C_1$–$C_4$-haloalkyl, aryl or other substituents which are inert under the reaction conditions, in which 1-methyl-3,5-diarylpyrazoles of the general formula II

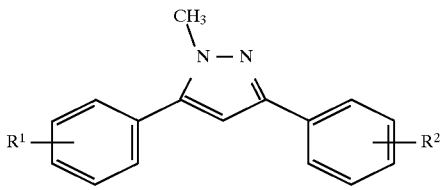

where $R^1$ and $R^2$ have the abovementioned meanings are reacted with a) methanol and $SO_3$,
b) methanol and sulfuric acid and/or
c) methanol and methylsulfuric acid at elevated temperatures.

1,2-Dimethyl-3,5-diarylpyrazolium methylsulfate compounds have been disclosed, for example 1,2-dimethyl-3,5-diphenylpyrazolium methylsulfate, which is employed as a selective herbicide against wild oats in barley and wheat and as fungicide against powdery mildew in winter wheat and barley. It is known to prepare the abovementioned compound by reacting 1-methyl-3,5-diphenylpyrazole with dimethyl sulfate in xylene (U.S. Pat. No. 3,882,142). A similar procedure is followed for the synthesis starting from 3,5-diphenylpyrazole (U.S. Pat. No. 3,910,949), where 3,5-diphenylpyrazole is first converted with sodium hydroxide to give the sodium pyrazolide, which reacts with dimethyl sulfate to give 1-methyl-3,5-diphenylpyrazole, which, in turn, is subsequently reacted with more dimethyl sulfate to give 1,2-dimethyl-3,5-diphenylpyrazolium methyl sulfate.

The disadvantage of the prior-art processes is the use of dimethyl sulfate, which is highly poisonous and relatively costly.

It was therefore an object of the present invention to provide a synthetic process in which the use of dimethyl sulfate is avoided in a simple and economical manner.

We have found that this object is achieved by the process according to the invention.

The radicals $R^1$ and $R^2$ in the compounds of the formulae I and II are preferably hydrogen. Suitable halogen radicals are fluorine, chlorine, bromine and iodine, preferably fluorine, chlorine and bromine. The nature of the substituents $R^1$ and $R^2$ is not of essential importance for the process according to the invention as long as they are inert under the reaction conditions.

The process according to the invention is carried out at elevated temperatures, in general at from 60° to 300 °C., preferably 100° to 250° C., in particular 120° to 180° C. It can furthermore be carried out under atmospheric pressure, under reduced pressure or under superatmospheric pressure.

The reactions of the compounds of the formula II

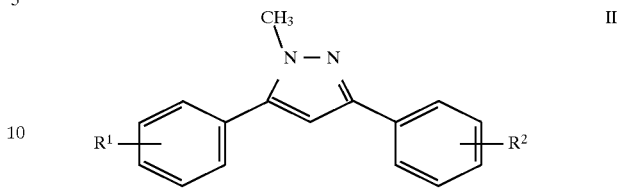

with methanol/$SO_3$, methanol/$H_2SO_4$ and methanol/methylsulfuric acid, which yield the compounds of the formula I

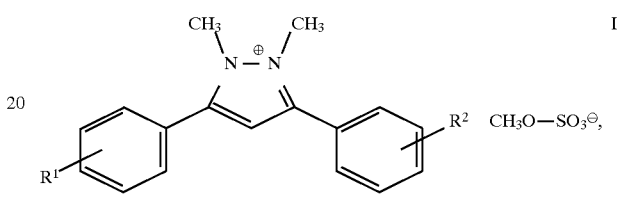

proceed as shown in the equations below:

a) $II+2CH_3OH+SO_3 \rightarrow I+H_2O$
b) $II+2CH_3OH+H_2SO_4 \rightarrow I+2H_2O$
c) $II+CH_3OH+CH_3OSO_3H \rightarrow I+H_2O$ The compound II is expediently reacted with $SO_3$ and/or its derivatives $H_2SO_4$ and/or $CH_3OSO_3H$ in such a ratio that the molar ratio of $SO_3$, $H_2SO_4$ and/or $CH_3OSO_3H$ to the compound II is 1.3:1 to 0.8:1, preferably 1.2:1 to 0.9:1, in particular 1.15:1 to 0.95:1. However, $SO_3$, $H_2SO_4$ and. $CH_3OSO3H$ can also be employed in an excess or in substoichiometric amount to exceed the range indicated above. However, it is particularly advantageous to carry out the reaction in a stoichiometric ratio, ie. in a molar ratio of approximately 1:1.

The third reactant, methanol, is generally employed in the process according to the invention in an excess above the stoichiometric amount, so that the methanol in this case acts as a reactant and simultaneously as the solvent. The molar ratio of the compound II employed to the methanol employed is, as a rule, 0.001:1 to 1:1, preferably 0.01:1 to 0.5:1.

In addition to using an excess of methanol as solvent, it is also possible to use other solvents which are inert under the reaction conditions, such as aliphatic or aromatic solvents. However, the use of an excess of methanol as the solvent is preferred.

When using sulfuric acid as a reactant, concentrated sulfuric acid (96–98% strength) is generally employed. Alternatively, the sulfuric acid can be of higher concentration, for example oleum with, for example, 20% of free $SO_3$, or less concentrated. The water, which is introduced at lower concentration when using sulfuric acid, is generally eliminated during the reaction together with the water formed during the reaction and, where appropriate, an excess of methanol.

The process according to the invention can be carried out for example in such a manner that the reactants are heated concomitantly to the reaction temperature, during which process methanol distills off. When the reaction temperature is reached, it is expedient to introduce more methanol by dropwise addition or in the form of a gas until the methylation is complete.

After the reaction has ended, working-up is carried out for example in such a manner that the reaction mixture is cooled and brought to crystallization. For purification, the crystal mixture can be digested or recrystallized using methanol or another solvent, such as ethanol, propanol, chlorinated hydrocarbons, toluene or xylene. The filtrates can be recirculated to the next methylation reaction, it being expedient beforehand to remove solvents—if used—with the exception of methanol.

The order in which the reactants are mixed with one another is of little importance in the process according to the invention; however, a procedure will generally be followed in which $SO_3$, $H_2SO_4$ or $CH_3O$—$SO_3H$ is added to a methanolic solution of the 1-methyl-3,5-diarylpyrazole II to be methylated, the solution is brought to the reaction temperature while evaporating methanol, and the resulting reaction mixture is treated with gaseous or liquid methanol in such a way that the reaction temperature can be maintained.

The process according to the invention is illustrated in greater detail by the examples which follow.

EXAMPLE 1

35.1 g (0.15 mol) of 1-methyl-3,5-diphenylpyrazole together with 80 g (2.5 mol) of methanol are introduced into a stirring apparatus. 13.2 g (0.165 mol) of $SO_3$ are subsequently added dropwise. The reaction solution is brought to 155° C. by distilling off methanol, and 320 g (10 mol) of methanol are metered in below the surface of the liquid in the course of 6 hours. Excess methanol and the water formed during the reaction are distilled off using a distillation head. After the reaction mixture has cooled, 55 g of a solidified melt are obtained. Recrystallization from 20 g of 1,1,1-trichloroethane gives 50 g of 1,2-dimethyl-3,5-diphenylpyrazolium methylsulfate with a content of 96.6% (HPLC) of m.p. 152°–154° C., which corresponds to a yield of 89.1% of theory.

EXAMPLE 2

46.8 g (0.2 mol) of 1-methyl-3,5-diphenylpyrazole together with 40 g (1.25 mol) of methanol are introduced into the reaction vessel. After 20.4 g (0.2 mol) of 96% strength sulfuric acid have been added, the reaction solution is brought to 160° C. by distilling off methanol. 640 g (20 mol) of methanol are metered in below the surface of the liquid in the course of 10 hours. After the reaction mixture has cooled, 73.5 g of a solidified melt are obtained. Recrystallization from 10 g of dichloromethane gives 67.7 g of 1,2-dimethyl-3,5-diphenylpyrazolium methylsulfate with a content of 99.4; (HPLC) of m.p. 158°–160° C., which corresponds to a yield of 93.4% of theory.

EXAMPLE 3

46.8 g (0.2 mol) of 1-methyl-3,5-diphenylpyrazole together with 40 g (1.25 mol) of methanol are introduced into the reaction vessel. After 19.4 g (0.19 mol) of 96% strength sulfuric acid have been added, the reaction solution is brought to 160° C. by distilling off methanol. 608 g (19 mol) of methanol are metered in below the surface of the reaction mixture in the course of 7.5 hours. After the mixture has been cooled to 70° C., 25 g of 1,2-dichloroethane are added, and the mixture is cooled to room temperature with stirring. The reaction mixture is filtered and washed with 12.5 g of 1,2-dichloroethane. 67.7 g of 1,2-dimethyl-3,5-diphenylpyrazolium methylsulfate with a content of 97.5% (HPLC) of m.p. 157°–159° C. are obtained, which corresponds to a yield of 91.7% of theory.

EXAMPLE 4

46.8 g (0.2 mol) of 1-methyl-3,5-diphenylpyrazole together with 40 g (1.25 mol) of methanol are introduced into the reaction vessel. After 23.5 g (0.21 mol) of methylsulfuric acid have been added, the reaction solution is brought to 155° C. by distilling off methanol. 480 g (15 mol) of methanol are metered in below the surface of the reaction mixture in the course of 5 hours. After the reaction mixture has cooled, 74 g of a solidified melt are obtained. After recrystallization from dichloromethane, 68.7 g of 1,2-dimethyl-3,5-diphenylpyrazolium methylsulfate with a content of 96% (HPLC) of m.p. 156°–158° C. are obtained, which corresponds to a yield of 91.6% of theory.

EXAMPLE 5

46.8 g (0.2 mol) of 1-methyl-3,5-diphenylpyrazole together with 40 g (1.25 mol) of methanol are introduced into the reaction vessel. After 22.5 g (0.22 mol) of 96% strength sulfuric acid have been added, the reaction solution is brought to 160° C. by distilling off methanol. 608 g (19 mol) of methanol are metered in below the surface of the reaction mixture in the course of 7.5 hours. After the mixture has cooled to 60° C., 10 g (0.31 mol) of methanol are added, and the mixture is cooled down to 10° C. At this temperature, the crystal slurry which has precipitated is filtered off. 68.1 g of 1,2-dimethyl-3,5-diphenylpyrazolium methylsulfate with a content of 97.3% (HPLC) of m.p. 157°–159° C. are obtained, which corresponds to a yield of 91.8% of theory.

46.8 g (0.2 mol) of 1-methyl-3,5-diphenylpyrazole, 40 g (1.25 mol) of methanol and 20.4 g (0.2 mol) of 96% strength sulfuric acid are added to the filtrate obtained, and the mixture is processed as described above. After working-up, 69.3 g of 1,2-dimethyl-3,5-diphenylpyrazolium methylsulfate with a content of 97.1% (HPLC) of m.p. 157°–159° C. are obtained, which corresponds to a yield of 93.5% of theory.

The filtrate obtained is recycled in the next experiment. After working-up, 68.3 g of 1,2-dimethyl-3,5-diphenylpyrazolium methylsulfate with a content of 97.8% (HPLC) of m.p. 157°–159° C. are obtained, which corresponds to a yield of 92.8% of theory.

After the filtrate has been recycled in the next experiment, 70.5 g of 1,2-dimethyl-3,5-diphenylpyrazolium methylsulfate with a content of 97.5% (HPLC) of m.p. 158°–160° C., which corresponds to a yield of 95.5% of theory, are obtained after working-up.

Over the four reactions, the total yield is 93.4% of theory.

EXAMPLE 6

20 g (0.074 mol) of 1-methyl-3-(4-fluorophenyl)-5-(3-methoxyphenyl)pyrazole together with 40 g (1.25 mol) of methanol are introduced into a stirred flask. 9.1 g (0.089 mol) of 96% strength sulfuric acid are subsequently added dropwise. The reaction solution is brought to 160° C. by distilling off with methanol. 512 g (16 mol) of methanol are subsequently added dropwise below the surface of the liquid in the course of 5 hours. Excess methanol and the water formed during the reaction are distilled off via a distillation head. After the reaction mixture has cooled to 70° C., 10 g of 1,2-dichloroethane are added, and the mixture is cooled down to 10° C. with stirring. The reaction mixture is filtered and washed with 5 g of 1,2-dichloroethane. 28.9 g of 1,2-dimethyl--3-(4-fluorophenyl)-5-(3-methoxyphenyl)-pyrazolium methylsulfate with a content of 88.6% of m.p. 172°–173° C., which corresponds to a yield of 84.8% of theory, are obtained.

We claim:

1. A process for the preparation of 1,2-dimethyl-3,5-diarylpyrazolium methylsulfates of the formula I

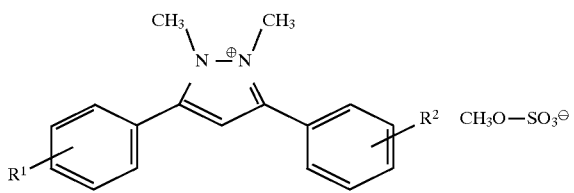

where $R^1$ and $R^2$ independently of one another are hydrogen, $C_1$–$C_4$-alkyl, $C_3$–$C_8$-cycloalkyl, $C_1$–$C_4$-alkoxy, halogen, nitro, $C_1$–$C_4$-haloalkyl or aryl, all of which are inert under the reaction conditions, which comprises reacting 1-methyl-3,5-diarylpyrazoles of the formula II

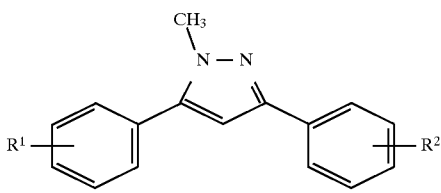

where $R^1$ and $R^2$ have the above-mentioned meanings with a) methanol and $SO_3$,
b) methanol and sulfuric acid or
c) methanol and methylsulfuric acid at elevated temperatures.

2. The process of claim 1 wherein a compound of the formula II is reacted with methanol and $SO_3$.

3. The process of claim 1 wherein a compound of the formula II is reacted with methanol and sulfuric acid.

4. The process of claim 1 wherein a compound of the formula II is reacted with methanol and methylsulfuric acid.

* * * * *